(12) United States Patent
Brackett (10) Patent No.: US 6,760,755 B1
(45) Date of Patent: Jul. 6, 2004

(54) IMAGING SYSTEM WITH USER-SELECTABLE PRESTORED FILES FOR CONFIGURING COMMUNICATION WITH REMOTE DEVICES

(75) Inventor: Charles Cameron Brackett, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 669 days.

(21) Appl. No.: 09/667,872

(22) Filed: Sep. 22, 2000

(51) Int. Cl.[7] .............................................. G06F 15/167
(52) U.S. Cl. ......................... 709/214; 709/220; 710/10; 345/735
(58) Field of Search ................................ 709/217, 219, 709/214, 220; 345/735; 710/8, 10

(56) References Cited

U.S. PATENT DOCUMENTS

| | | | | |
|---|---|---|---|---|
| 5,564,109 A | * | 10/1996 | Snyder et al. .................. 710/8 |
| 5,897,498 A | * | 4/1999 | Canfield et al. ............. 600/437 |
| 6,101,407 A | * | 8/2000 | Groezinger ................. 600/407 |
| 6,260,021 B1 | * | 7/2001 | Wong et al. .................... 705/2 |
| 6,275,869 B1 | * | 8/2001 | Sieffert et al. .............. 709/321 |
| 6,306,089 B1 | * | 10/2001 | Coleman et al. ............ 600/437 |
| 6,351,547 B1 | * | 2/2002 | Johnson et al. ............. 382/128 |
| 6,388,687 B1 | * | 5/2002 | Brackett et al. ............ 345/810 |
| 6,417,870 B1 | * | 7/2002 | Brackett et al. ............ 345/771 |
| 6,477,589 B1 | * | 11/2002 | Suzuki et al. .................. 710/18 |
| 6,519,632 B1 | * | 2/2003 | Brackett et al. ............ 709/219 |
| 6,574,518 B1 | * | 6/2003 | Lounsberry et al. .......... 700/90 |
| 6,587,959 B1 | * | 7/2003 | Sjolander et al. .............. 714/4 |
| 6,618,060 B1 | * | 9/2003 | Brackett ..................... 345/810 |
| 2002/0062366 A1 | * | 5/2002 | Roy et al. ................... 709/224 |

* cited by examiner

Primary Examiner—Hosain Alam
Assistant Examiner—Oanh Duong
(74) Attorney, Agent, or Firm—Ostrager Chong & Flaherty LLP (57) ABSTRACT

Method and apparatus for configuring an imaging system for communication with different remote devices having different requirements. A field engineer selects a prestored configuration file for a particular device from a configuration file library stored on the imaging system hard disk. The selection is made by selecting from a drop-down pick list of equipment identified by make and model. The pick list itself is constructed from information extracted from the configuration file library. The configuration data in the selected configuration file is used to construct a new configuration file, which is later saved to the hard disk. If the device is activated, a portion of the selected configuration file is also copied to an Attribute Control File, which is later saved to the hard disk. The installed configuration files and the Attribute Control Files for activated devices are then read into system memory when the imager is rebooted. Each prestored configuration file includes presets which constitute the best imaging and formatting settings for the particular device as determined by specialists at a central service facility. The configuration file will also include the attribute information for the particular remote device.

21 Claims, 8 Drawing Sheets

DEVICE CONFIGURATION          PAGE    1 of 11

NAME    [CTN]
IP ADDR  [3].[28].[127].[89]                    AE TITLE   [DICOM_STORAGE]
PORT    [4080]   COLOR [MIXED]                  DEVICE TYPE [STORAGE]
RETRIES [1]      RETRY INTERVAL [10] SEC        TIMEOUT  [10] SEC — 48
ECHO [ECHO ON]   ACTIVATE [YES]—50              XFER SYNTAX [IMP LE]
PRINTER SETUP
 FORMAT
 SIZE               ORIENTATION
 COPIES             MEDIA TYPE
 PRIORITY           BORDER
 MIN DENSITY        EMPTY
 TRIM               MAX DENSITY
 MAGNIFICATION      DESTINATION
 SMOOTH
 FILM SESSION LABEL
CONFIGURATION STRING
WORKLIST SETUP                       STORAGE SETUP
 POLLING RATE [0] MINUTES              TYPE [AUTOMATIC]
                                       LIVE IMAGING [OFF]
                                       ROI   SIZE TO PAGE
TKBL/RET TO POSITION   SET TO SELECT         EXIT    TO SAVE

Worklist Setup

| Display Order | | Search Field | Criteria |
|---|---|---|---|
| DISPLAY | 1 | First Name | |
| DISPLAY | 2 | Last Name | |
| DISPLAY | 4 | Exam Start Date | 3/10/1999 — 68 |
| SEARCH | | Exam Start Date Range | 9 days |
| SEARCH | | Modality | |
| SEARCH | | Schedule Description | |
| SEARCH | | Station Name | |
| SEARCH | | Location | |
| SEARCH | | Request Procedure ID | |
| SEARCH | | Accession Number | |
| SEARCH | | Admission ID | |
| SEARCH | | AE Title | |
| DISPLAY | 3 | Patient ID | |
| SEARCH | | Date of Birth | 0/0/0 |
| SEARCH | | Gender | |
| SEARCH | | Req. Proc. Desc. | |

64 — 66

FIRST NAME    LAST NAME    PATIENT ID    START DATE

TKBL/RET to position    SET to select    ROI Size to page
                                          EXIT to save

FIG. 8

DEVICE ACTIVATION

| | NAME | ACTIVE |
|---|---|---|
| 1 | CTN | YES —60 |
| 2 | PRINTER B | YES |
| 3 | STORAGE A | YES |
| 4 | STORAGE B | NO |
| 5 | PRINTER X | NO |
| 6 | PRINTER Y | NO |
| 7 | | NO |
| 8 | | NO |
| 9 | | NO |
| 10 | | NO |
| 11 | | NO |
| 12 | | NO |
| 13 | | NO |
| 14 | | NO |
| 15 | | NO |
| 16 | | NO |
| 17 | | NO |
| 18 | | NO |
| 19 | | NO |
| 20 | | NO |

TKBL/RET TO POSITION    SET TO SELECT    ROI SIZE TO PAGE
                                         EXIT TO SAVE

IMAGING SYSTEM WITH USER-SELECTABLE PRESTORED FILES FOR CONFIGURING COMMUNICATION WITH REMOTE DEVICES

FIELD OF THE INVENTION

This invention generally relates to imaging systems which communicate with remote devices via networks. In particular, the invention relates to the transfer of digital images from an imaging system to remote devices for archiving, viewing and/or printing. The invention also relates to retrieval by an imaging system of worklist data from a worklist broker via a network.

BACKGROUND OF THE INVENTION

Conventional ultrasound imagers create two-dimensional images of biological tissue by scanning a focused ultrasound beam in a scan plane and for each transmitted beam, detecting the ultrasound wave energy returned along a respective scan line in the scan plane. A single scan line (or small localized group of scan lines) is acquired by transmitting focused ultrasound energy at a point, and then receiving the reflected energy over time. A B-mode ultrasound image is composed of multiple image scan lines. The brightness of a pixel on the display screen is based on the intensity of the echo returned from the biological tissue being scanned. The outputs of receive beamformer channels are coherently summed to form a respective pixel intensity value for each sample volume in the scanned object. These pixel intensity values are log-compressed, scan-converted and then displayed as a B-mode image of the anatomy which was scanned.

If the ultrasound probe is swept over an area of body, a succession of image frames (corresponding to spaced slices intersecting the body being examined) can be displayed on the monitor. In one type of ultrasound imaging system, a long sequence of the most recent images are stored and continuously updated automatically in a cine memory on a first-in, first-out basis. The cine memory is like a circular image buffer that runs in the background, capturing image data that is displayed in real time to the user. The cine memory acts as a buffer for transfer of images to digital archival devices via the host computer. When the user freezes the system (by operation of an appropriate device on an operator interface), the user has the capability to view image data previously captured in cine memory. The image loop stored in cine memory can be reviewed on the display monitor via trackball control incorporated in the operator interface, and a section of the image loop can be selected for hard disk storage. Any acquired or projected image can be stored internally on the system hard disk or on a magneto-optical disk (MOD) inserted in a disk drive.

In addition to storing images internally, modern imaging systems need to be able to transfer images to various types of remote devices via a communications network. To successfully transfer images, the relevant networking features of the imager must be compatible with the networking features of the destination remote device. In particular, the imager must place the data to be transferred in a format which can be handled by the destination remote device. An attempt to accomplish the foregoing is the adoption of the DICOM (Digital Imaging and Communications in Medicine) standards, which specify the conformance requirements for the relevant networking features. The DICOM standards are intended for use in communicating medical digital images among printers, workstations, acquisition modules (such as an ultrasound imaging system) and file servers. The acquisition module is programmed to transfer data in a format which complies with the DICOM standards, while the receiving device is programmed to receive data which has been formatted in compliance with those same DICOM standards.

The DICOM system is based on the client/server concept. The device which uses a service (on objects) is the client device, while the device which provides the service is the server device. The client device is referred to as a Service Class User (SCU), while the server device is referred to as a Service Class Provider (SCP). The SCU sends a Service Request to the SCP over a local area network (LAN). The SCP sends back a response to the SCU over the same LAN. If the response is affirmative and a communications syntax is agreed upon, an association between the SCU and the SCP is opened and data can be transferred between the two devices. In the DICOM system a device is not limited to one role: it can be both SCU and SCP at different times.

The DICOM system is designed to facilitate the communication of digital images of different types, e.g., X-ray, computerized tomography, magnetic resonance and ultrasound imaging. In an ultrasound imager having conventional DICOM capability, three local real-world activities occur: Image Send, Image Print and Remote Verification. Image Send and Image Print can be done in either automatic or manual mode. Verification of remote DICOM devices configured on the ultrasound imager is performed when the imager is powered up or when requested by the system operator.

All DICOM activities are handled in a queued manner by application software running on a host computer incorporated in the imager. In one type of ultrasound imager, the user can select any image in cine memory to be sent in DICOM format via a LAN to a remote device having DICOM capability. The host computer of the ultrasound imaging system is programmed with DICOM system software which facilitates transmission of image frames from the cine memory to the remote DICOM device via the host computer hard disk and the LAN.

In the conventional ultrasound imager, Image Send can be used in automatic or manual mode, depending on the user configuration. When automatic mode is configured, console keys are used to capture the image and to store it on the hard disk. The request is queued to a DICOM queue manager (preferably implemented in software), which requests an association with the destination remote device. After the association with the remote device has been opened, the queue manager "pushes" the image to the remote device without user intervention. The transfer is done in the background while scanning or other operator activities continue. In manual mode, the captured images are archived on the hard disk or on a MOD during the exam(s). Upon completion of the exam(s) the images are tagged using an archive menu and queued to any of the network devices that have been configured on the imager. The images are sent sequentially in the background while scanning or other operator activities proceed. Image Print works much the same way as Image Send, in both automatic and manual modes, the only difference being that the destination device is a printer.

In order to accomplish image transfer, the ultrasound imaging system must know the configuration of the destination remote device prior to attempting to communicate with that device. The configuration data for the destination remote device is typically inputted to the ultrasound imager during software installation by a field engineer (e.g., by inserting an installation disk), although an imaging system can be configured at any time. The constructed configuration file is stored on the hard disk and read into system memory each time the system powers up. When the imager receives an instruction to transmit data to a particular remote device from the system operator, the imager software converts the image data to be transferred into the DICOM format required by the destination remote device, based on the configuration data for that device stored in system memory. The imager also sends a request over the network to the destination remote device to open an association, i.e., to connect the imager to the destination remote device. If the remote device responds in the affirmative, the imager and remote device then agree on which device will act as the server and which as the client. The ultrasound imager also selects the appropriate encoding syntax from those accepted by the remote device. Other communication parameters are also negotiated.

After the DICOM communications protocol has been settled, the association is opened and the imager attempts to send the DICOM-formatted image file (object) to the remote device via the network. The transfer is done in the background while scanning or other operator activities continue. If the remote device is a storage device, each image file is transferred singly in response to a Send request inputted by the operator. If the remote device is a printer configured to print multi-image film, then a number of images are accumulated to make up a multi-image film and an association is opened in response to a Send instruction when a number of images sufficient to fill the multi-image film have been accumulated.

The remote device to which the ultrasound imager sends data can be a printer, a storage device or other device. If the operator interface of the imager has only one configurable Print/Store button, then that button will be configured to initiate data transfer to the destination remote device. The configuration data for the remote device will indicate the type of device to the imager and then the imager will format the data being transferred accordingly. If the operator interface has multiple Print/Store buttons, then each button can be configured to initiate data transfer to a respective remote device. Data transfer to any one of those configured remote devices can then be initiated by pressing the appropriate Print/Store button.

In addition to the digitized image (i.e., pixel data), the DICOM object transferred from the ultrasound imager also includes attribute information extracted from the configuration file. For example, the attribute information may include patient attributes (e.g., patient name and patient identification number), exam attributes (e.g., exam description and exam date), series attributes (e.g., modality type and series date), and image attributes (e.g., image type and numbers of rows and columns). Each attribute has a name, a value representation and a tag. A tag is a number unique to the attribute, e.g., (0040,0100), and is used to identify the attribute. (Different systems use different tags for the same attribute name, which gives rise to incompatibility, as described in more detail hereinafter.) The value representation defines what type of value the attribute can have (e.g., a 64-character string, binary data, etc.).

In accordance with DICOM standards, there are three types of attributes. Type 1 comprises attributes which are mandatory and must always be present with a value; Type 2 comprises attributes which are mandatory but are allowed to be empty; and Type 3 comprises attributes which are optional and are also allowed to be empty. An incompatibility between two devices may arise, for example, if the receiving device requires that a Type 3 attribute be transmitted while the sending device does not include that attribute in its transmission. As a result, even if both devices are configured in accordance with current DICOM standards, the data transfer cannot occur. Thus, even mutual conformance to DICOM standards does not guarantee that two devices can be compatibly connected to each other.

In accordance with a further aspect of the DICOM system as currently implemented, an ultrasound imaging system can retrieve a worklist from a Radiology Information System (RIS) at a hospital via a local area network (LAN). The retrieved worklist may, e.g., comprise all patients to be examined on a particular day using that particular ultrasound imager. The worklist includes the following information for each patient: name, identification number, sex, birth date, accession number, study data, etc. The information retrieval is initiated by the ultrasound imager. A user-interactive Worklist Setup menu is provided which allows the user to select one or more search fields and enter search criteria for each field. The search results are received from the remote worklist broker by the imaging system and stored in memory. This feature gives the system operator the ability to create a local patient list on the imaging system. The user can then select any patient from the worklist for an examination. Selecting a patient from the worklist means that all of the data associated with that patient, which was retrieved from the worklist broker (remote device), will be included with every image of that patient which is stored in image files on the hard disk. Those images are subsequently converted into DICOM objects for transfer to remote printers and storage devices.

Because the DICOM capability is implemented in software, these features of the ultrasound imaging system can be readily upgraded. One goal of such upgrades is to increase the efficiency of the system operator by making the system simpler to operate, e.g., by requiring fewer manipulations to activate a particular operation. Another goal of system upgrades is to increase the ability of the imager to connect rapidly, efficiently and reliably to remote devices on the network, i.e., to increase connectivity.

A known imaging system comprises means for turning off or turning on any DICOM attribute to facilitate communication with a particular remote device. This is accomplished by providing an Attribute Control File which is programmable. However, this feature can be utilized only by the few persons who know which DICOM attributes to turn off. The problem is further complicated because some of these attributes are dependent on other attributes and are order sensitive. Therefore, turning one attribute off without turning off an attribute dependent on the first attribute or changing the order of a sequence of attributes can cause even more problems. This complex arrangement of attributes and their dependencies are described in a 14-volume reference set known as the DICOM 3.0 standard. Service people do not have a copy of this reference set and will not get a copy of this set, because it is very expensive and too complex for the service engineer.

Thus there is a need for a method to simplify the process of configuring an imaging system to a communicate with a new DICOM storage device, printer, or worklist broker. Today, this process is manual in that when the field engineer goes to a site to configure an imaging system to communicate with a newly installed DICOM device, the field engineer will go to a Device Configuration screen and manually fill out the configuration information for the remote device being added. The configuration information, including what attributes are mandatory, varies from device to device and even from revision to revision of the same type of devices. There is a need for a simple method whereby a field engineer or other system user can configure the attributes which an imaging system will send to a particular remote device without knowing or inquiring which attributes that particular remote device requires.

SUMMARY OF THE INVENTION

The present invention is incorporated in an imager which is programmed with at least one task for constructing objects to be transferred to a remote device. The imager may comprise multiple tasks for communicating with a respective multiplicity of remote devices. Each task is configurable by the user to construct objects compatible with a particular remote device, e.g., a storage device or printer. Each configured remote device can then be "activated", with the understanding that the term "activation", as used in this context, means that the imager has a task configured for that remote device, not that the remote device itself is in any sense remotely activated by the imager. In accordance with the preferred embodiment, the tasks are configured to comply with DICOM standards.

In accordance with the DICOM standard, a DICOM task can be designed to convert an image file, comprising image frame data and attribute data, into a DICOM-formatted object, also comprising image frame and attribute data. That DICOM object must conform not only to the DICOM standards and the imaging and formatting requirements of the particular device, but also to the attribute requirements (i.e., tags) of the particular remote device destined to receive that DICOM object. After construction, the DICOM object can be sent to the destination storage device or printer. In addition, another DICOM task in the imaging system can be designed to send a modality worklist query to a remotely located device, e.g., a worklist broker. That query must also conform to DICOM standards and be compatible with the formatting and attribute requirements of the receiving device.

The imaging system incorporating the present invention has a separate Attribute Control File for each different activated configured remote device. Each Attribute Control File, in ASCII format, is a mapping of which attributes should be included and which attribute tags should be used in every image or worklist query transmitted to the remote device associated with that Attribute Control File. Each DICOM task will convert each image file or worklist query file into a DICOM object comprising the attribute data dictated by the Attribute Control File associated with the corresponding DICOM task. A host computer of the imaging system is programmed with an Attribute Control Engine which controls the inclusion of particular attributes and attribute tags in the DICOM objects constructed by each DICOM task. In particular, in response to queries from a DICOM task, the Attribute Control Engine will instruct that DICOM task concerning which attributes and what attribute tags should be included in the DICOM object being constructed. The Attribute Control Engine in turn obtains that information from the Attribute Control File associated with that DICOM task.

In accordance with the preferred embodiment of the present invention, a field engineer is able to select a prestored configuration file for a particular device from a configuration file library stored on the imaging system hard disk. The field engineer selects a configuration file by interacting with a graphical user interface, i.e., by selecting from a drop-down pick list of equipment identified by make and model. The pick list itself is constructed from information extracted from the configuration file library. The data in the selected configuration file from the library is supplemented, and optionally modified, to create a new configuration file which is copied into or installed at a different address on the hard disk when installation is finished. During subsequent powering up of the imaging system, the new configuration file will be copied into system memory, and an attribute section of the new configuration file will be copied to an Attribute Control File in system memory, for use during system operation.

In accordance with the preferred embodiment of the invention, each prestored configuration file includes presets which constitute the best imaging and formatting settings as determined by specialists at a central service facility. This reduces the amount of time which a field service engineer must spend to adjust the settings by trial and error when a new imaging system is installed or when an existing imaging system is being configured to communicate with a new remote device. The presets may include certain image quality settings, image format settings, and so forth. Once the best settings have been determined for a particular device, the service center personnel will create a configuration file for that device. This configuration file will also include the attribute information for the particular remote device. The prestored file will serve as a default configuration for that remote device. As many files as possible will be created to form a library of configuration files. This library of files can be modified at a subsequent time if need be.

In accordance with the preferred embodiment, the configuration file library will be placed on the install disks to be installed with every new installation. Alternatively, the configuration file library can be added later. The library will preferably include configuration files for all commercially available devices which could conceivably be connected to a DICOM communications network. Preferably the field engineer can adjust the prestored settings if necessary.

Although the preferred embodiment of the invention is disclosed below in the context of imaging systems which communicate with remote devices using the DICOM standard, it will be appreciated that the broad concept of the invention has application with any digital image communications standard or protocol that requires configuration of the imaging device as a function of different requirements of different receiving devices.

DETAILED DESCRIPTION OF THE PREFERRED EMBODIMENTS

Figure 1:
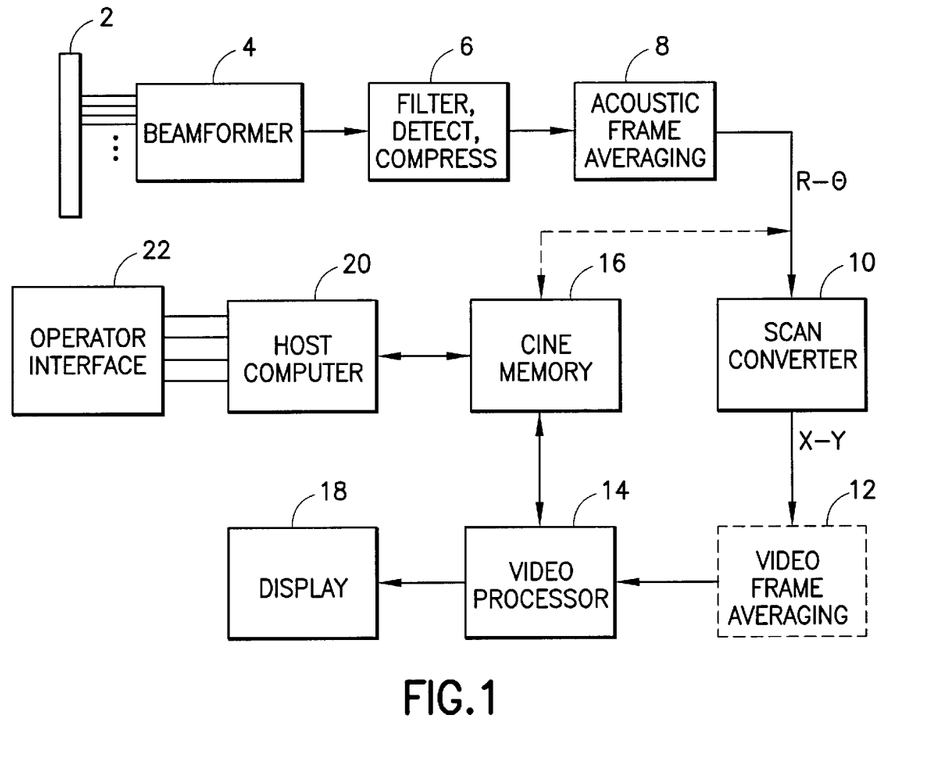
FIG. 1 is a block diagram generally depicting portions of a conventional ultrasound imaging system of the type which can be programmed to have DICOM capability.

FIG. 1 shows a conventional computerized ultrasound imaging system which can be programmed to communicate with remote devices over a network in conformance with the DICOM standards The type of imaging system depicted in FIG. 1 creates two-dimensional B-mode images of tissue in which the brightness of a pixel is based on the intensity of the echo return. The basic signal processing chain is as follows.

An ultrasound transducer array 2 is activated to by a transmitter in a beamformer 4 to transmit an acoustic burst which is focused at a point along a scan line. The return RF signals are detected by the transducer elements and then dynamically focused to form a receive beam by a receiver in the beamformer 4. The receive beamformer output data (I/Q or RF) for each scan line is passed through a B-mode processing chain 6, which preferably includes demodulation, filtering, envelope detection, logarithmic compression and edge enhancement.

Depending on the scan geometry, up to a few hundred receive vectors may be used to form a single acoustic image frame. To smooth the temporal transition from one acoustic frame to the next, some acoustic frame averaging 8 may be performed before scan conversion. In general, the log-compressed display data is converted by the scan converter 10 into X-Y format for video display. On some systems, frame averaging may be performed on the X-Y data (indicated by dashed block 12) rather than the acoustic frames before scan conversion, and sometimes duplicate video frames may be inserted between acoustic frames in order to achieve a given video display frame rate. The scan-converted frames are passed to a video processor 14, which maps the video data using a gray-scale mapping. The gray-scaled image frames are then sent to a video monitor 18 for display.

System control is centered in a host computer 20, which accepts operator inputs through an operator interface 22 and in turn controls the various subsystems. (In FIG. 1, only the image data transfer paths are depicted.) The operator interface comprises a keyboard, a trackball, a multiplicity of pushbuttons, and other input devices such as sliding and rotary knobs.

During imaging, a long sequence of the most recent images are stored and continuously updated automatically in a cine memory 16. Some systems are designed to save the R-θ acoustic images (this data path is indicated by the dashed line in FIG. 1), while other systems store the X-Y video images. The image loop stored in cine memory 16 can be reviewed via trackball control, and a section of the image loop can be selected for hard disk storage.

Figure 2:
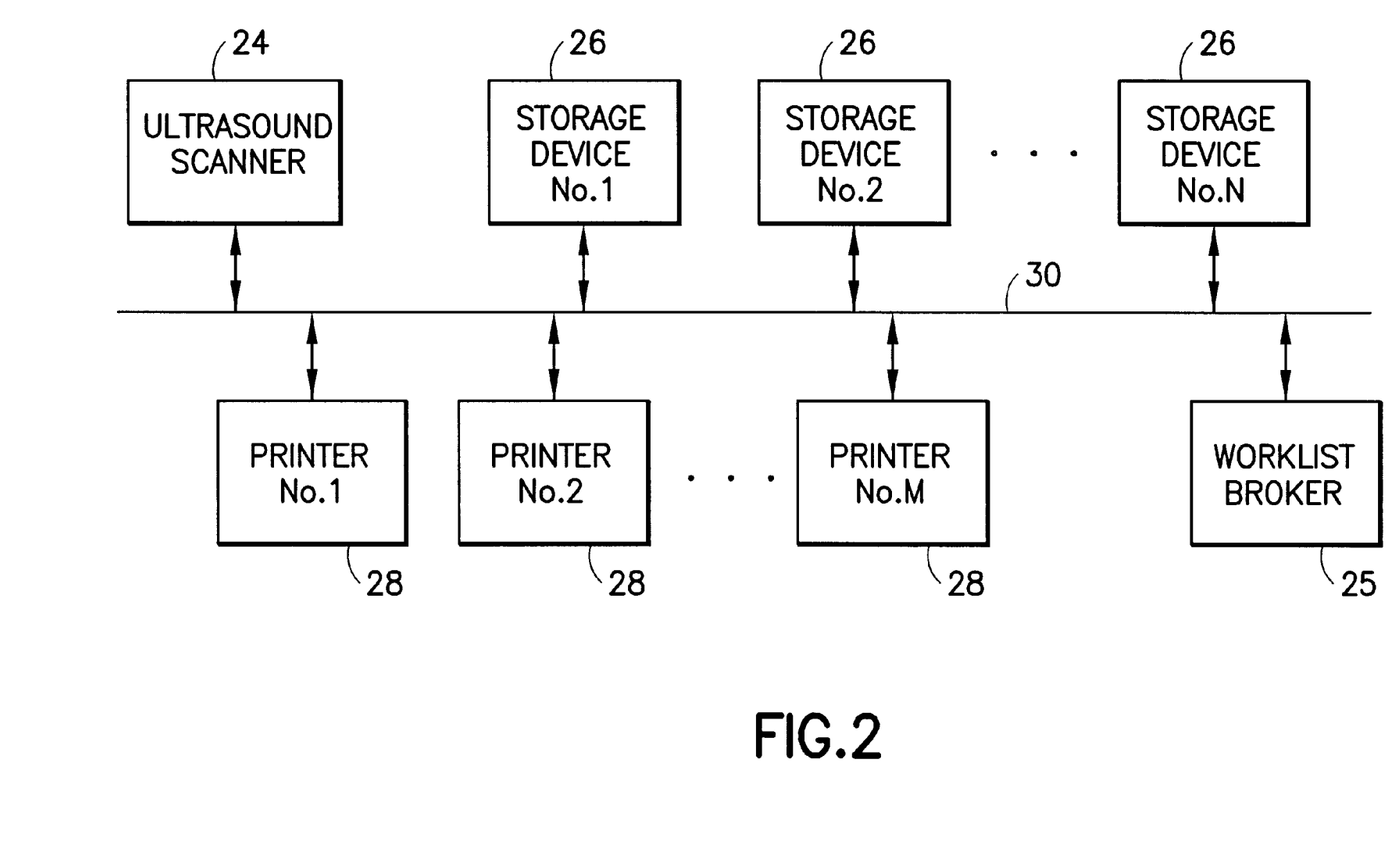
FIG. 2 is a block diagram generally depicting a typical DICOM network.

FIG. 2 generally depicts a simplified DICOM network having an ultrasound scanner 24, a worklist broker (e.g., an RIS) 25, N storage devices 26, and M printing devices 28, all connected to a local area network (LAN) 30. It will be readily appreciated that this diagram represents a simplified example of a DICOM network and that an actual DICOM network in the real world will have many more devices connected to the LAN, including modalities other than ultrasound imaging systems. The preferred embodiment of the invention is disclosed in the context of an imager (scanner) having the built-in capability to communicate with any one or more of the devices 25, 26 and 28 in conformance with the DICOM requirements. As used herein, the term "storage device" includes, but is not limited to, a picture archiving and communications system (PACS) having a viewing station.

Figure 3:
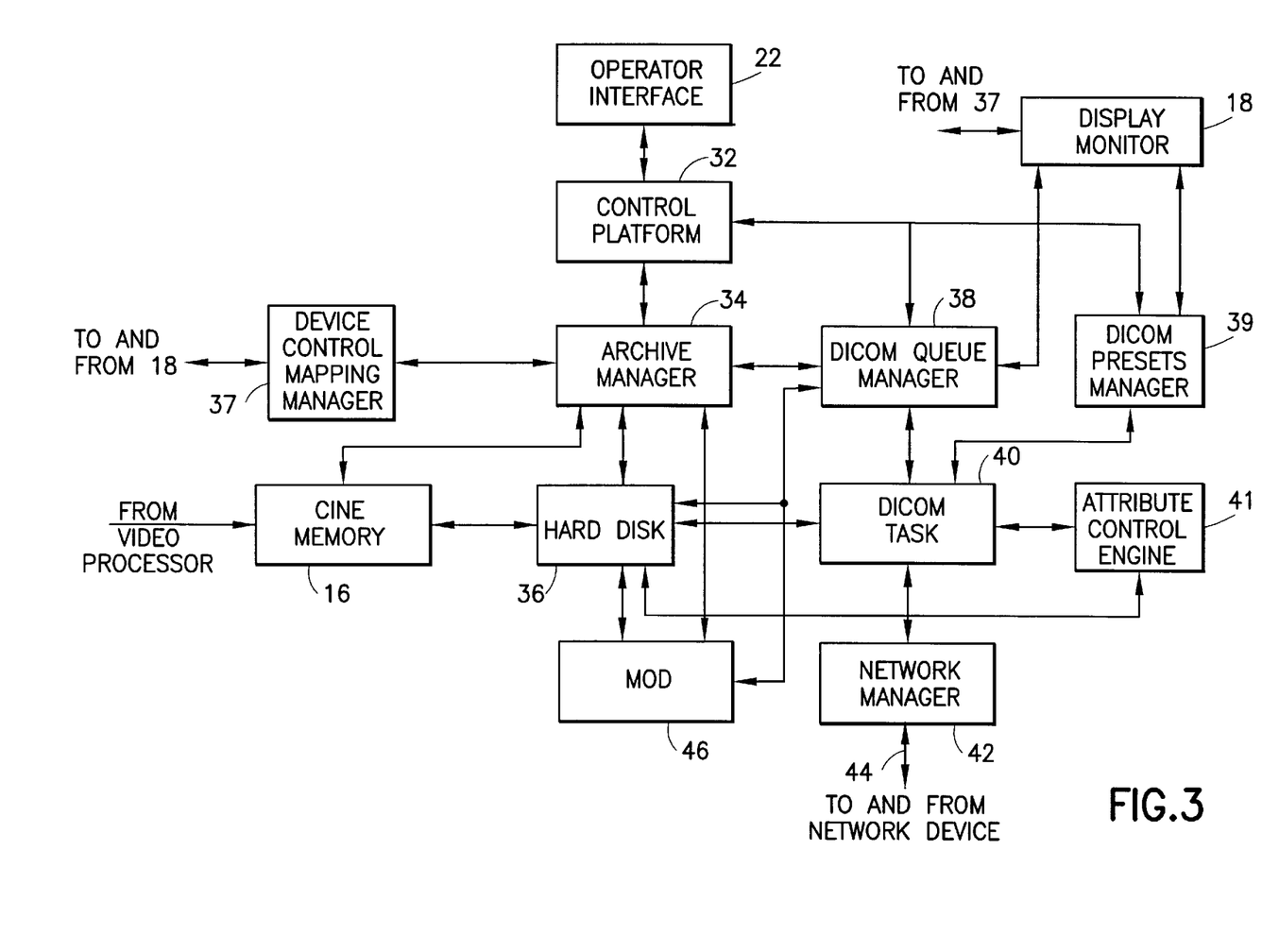
FIG. 3 is a block diagram generally depicting portions of the hardware and software of an ultrasound imaging system having DICOM capability.

A portion of an ultrasound imager which can be programmed to incorporate the present invention is generally depicted in FIG. 3. At the outset it should be appreciated that all of the blocks depicted in FIG. 3, with the exceptions of the cine memory 16, the display monitor 18, the operator interface 22 and the hard disk 36, are preferably, but not necessarily, incorporated in the host computer (depicted in FIG. 1 as block 20). It should be further appreciated that blocks 32, 34, and 37–42 in FIG. 3 are preferably, but not necessarily, implemented as software.

In the system depicted in FIG. 3, commands inputted via the operator interface 22 are detected and processed by a control platform 32. In return, the control platform will provide signals to the operator interface which activate various visual indicators on the operator interface to indicate the status of various functions. In response to manipulation of the appropriate key or appropriate set of keys by the operator, the DICOM presets manager 39 will display a "Device Configuration" menu (shown in FIG. 4) on the display monitor 18. In the past, a person undertaking to configure the imager for a particular remote device (e.g., the storage device named "CTN" in FIG. 4) would enter the configuration in the appropriate fields on the Device Configuration menu via the operator interface. Depending on whether the device being configured was a printer, a storage device or a worklist broker, the Device Type field 48 on the Device Configuration menu would be filled in with either a "Printer", a "Storage" or a "Worklist" entry. A separate page of the Device Configuration menu is filled in for each remote device which the operator wishes to configure.

The imager shown in FIG. 3 is designed to communicate with a configured remote device only if that device has been "activated". Activation causes the DICOM presets manager 39 to configure one of a multiplicity of DICOM tasks 40 in accordance with configuration data entered into the system for the associated remote device. That particular DICOM task will thereafter remain configured for that type of remote device until reconfigured for a different device. Other DICOM tasks are configured for other remote devices.

Figure 8:
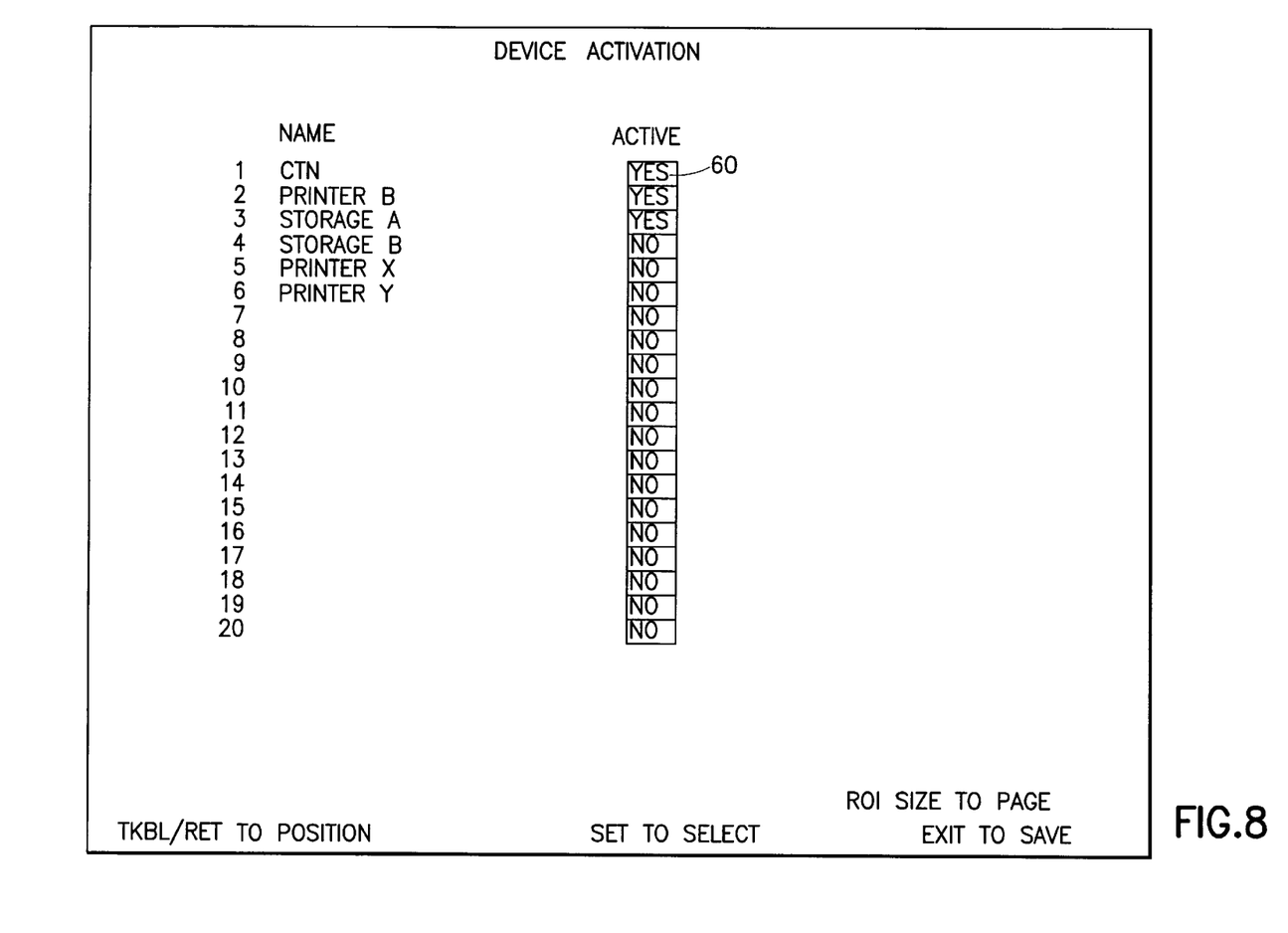
FIG. 8 is a schematic reproducing a "Device Activation" menu which can be used to activate selected configured remote devices in the imaging system partially depicted in FIG. 5.

One way of activating a remote device is to click on the Activate field 50 on the Device Configuration menu (see FIG. 4) to toggle the "Activate" state on. A second click on field 50 will toggle the "Activate" state off, and so forth. Alternatively, the operator can call up the Device Activation menu shown in FIG. 8, which is sent to the display monitor by the DICOM presets manager 39. The Device Activation menu comprises a list of the names of all configured remote devices, whether activated or not. A respective Activation field 60 is associated with each named device. The operator is able to activate or deactivate each configured device by simply clicking on its associated Activation field. [As used herein, the term "clicking" includes, but is not limited to highlighting a field by manipulation of a trackball and then pressing a Set key on the operator interface.] A Yes or No is displayed in the Activation field to provide a visual indication of whether the remote device is activated. FIG. 8 assumes that the remote devices named CTN, Printer B and Storage A have been configured and activated, while the remote devices named Printer X, Printer Y and Storage B have been configured and not activated.

Referring again to FIG. 3, the imaging system is equipped with a plurality of Print/Store buttons on the operator interface 22. Each Print/Store button can be configured by the device control mapping manager 37 to initiate image transfer to more than one remote device, e.g., when a particular Print/Store button is pressed, the computer will send the corresponding acquired image to all activated remote devices configured for that button. The device control mapping manager is programmed to retrieve a Device Control menu, which is a virtual representation of the various configurations for the Print/Store buttons, from the hard disk 36 and send it to the display monitor 18. Each control state can be configured so that the data of the acquired image is expressed as either color intensity values or gray-scale intensity values; so that the acquired image will be stored on the hard disk or the MOD; so that the acquired image will be transferred to one or more activated remote devices; or any combination of these options. Each Print/Store button configuration can be set via the operator interface. For each remote device configured to a particular Print/Store button, pressing that button after freezing an image will cause the associated DICOM task to retrieve an image file having a copy of that image from the hard disk and convert that image file to a DICOM object compatible with the associated remote device.

The device control mapping manager 37 constructs a mapping of DICOM tasks (configured for respective remote devices) to Print/Store buttons. In other words, when the operator interacts with the Device Control menu (not shown) to configure a Print/Store button to a particular remote device, the device control mapping manager then identifies the DICOM task corresponding to that remote device and includes it in the device control mapping. The device control mapping manager 37 provides the device control mapping to the archive manager 34. When the archive manager later receives a posting from the control platform 32 that a particular Print/Store button has been pressed, the archive manager 34 will then refer to the device control mapping and determine the DICOM tasks associated with that button from the mapping. The archive manager 34 then advises the DICOM queue manager 38 which DICOM tasks 40 need to construct objects incorporating the selected image frame. The DICOM queue manager 38 then copies that image file once for each task and, if the remote devices are storage devices or single-image printers, adds a job element to the Active Queue of each task. For multi-image printers, the DICOM queue manager 38 need only add another image file name to the Image File Name field of an existing job element in the queue.

Although FIG. 3 depicts only one DICOM task, in accordance with the preferred embodiment, the imager is typically programmed with multiple DICOM tasks. Typically one DICOM task is dedicated to worklist management and ten DICOM tasks are configured to convert image files into either DICOM print objects or DICOM storage objects. In response to pressing of a Print/Store button which is configured for multiple remote devices, a corresponding multiplicity of DICOM tasks will be started substantially simultaneously. These concurrently running tasks are performed using conventional multi-tasking principles.

Figure 4:
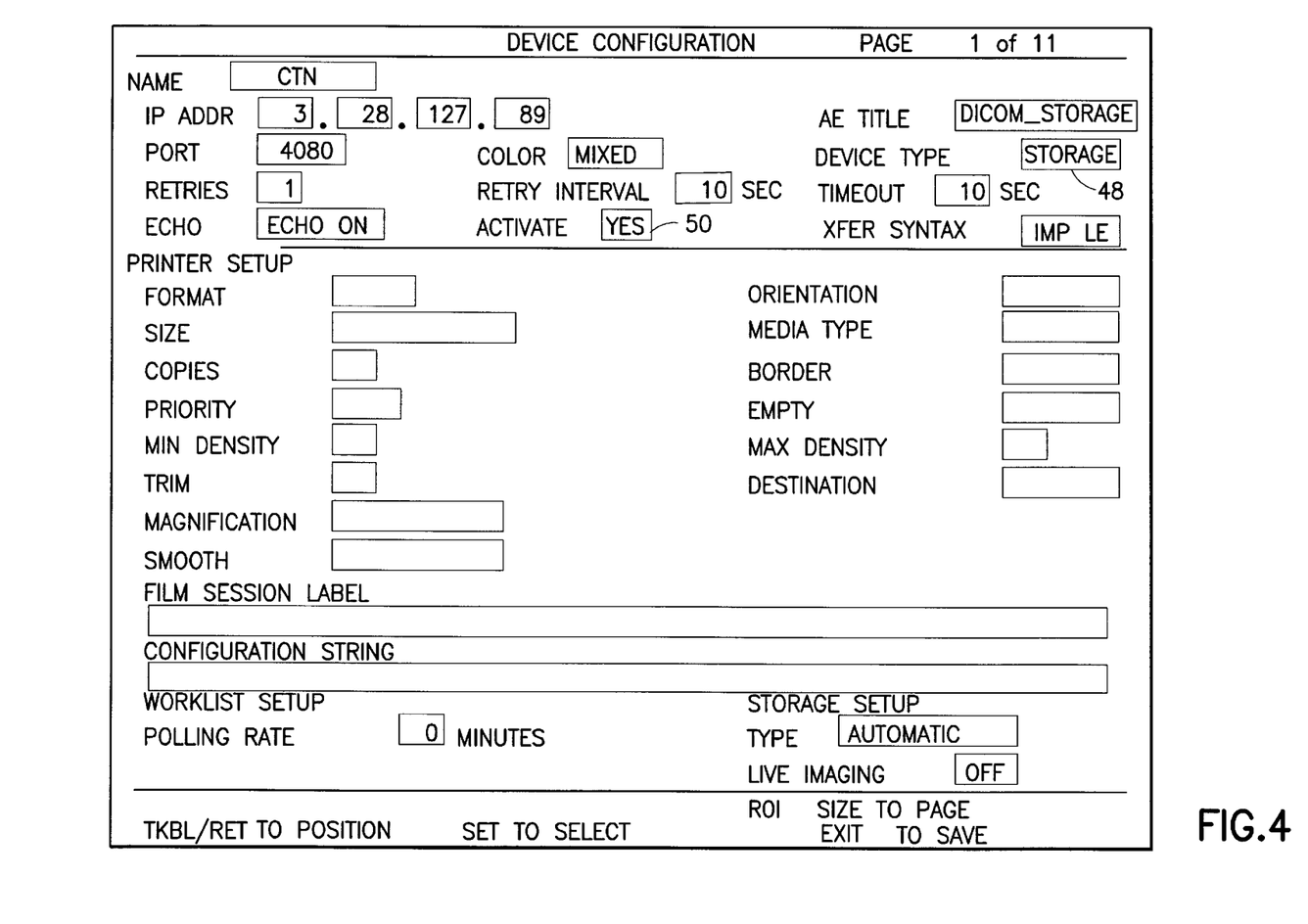
FIG. 4 is a schematic reproducing a "Device Configuration" menu which can be called up on the display monitor during configuration of the imaging system in accordance with the preferred embodiment of the present invention.
Figure 5:
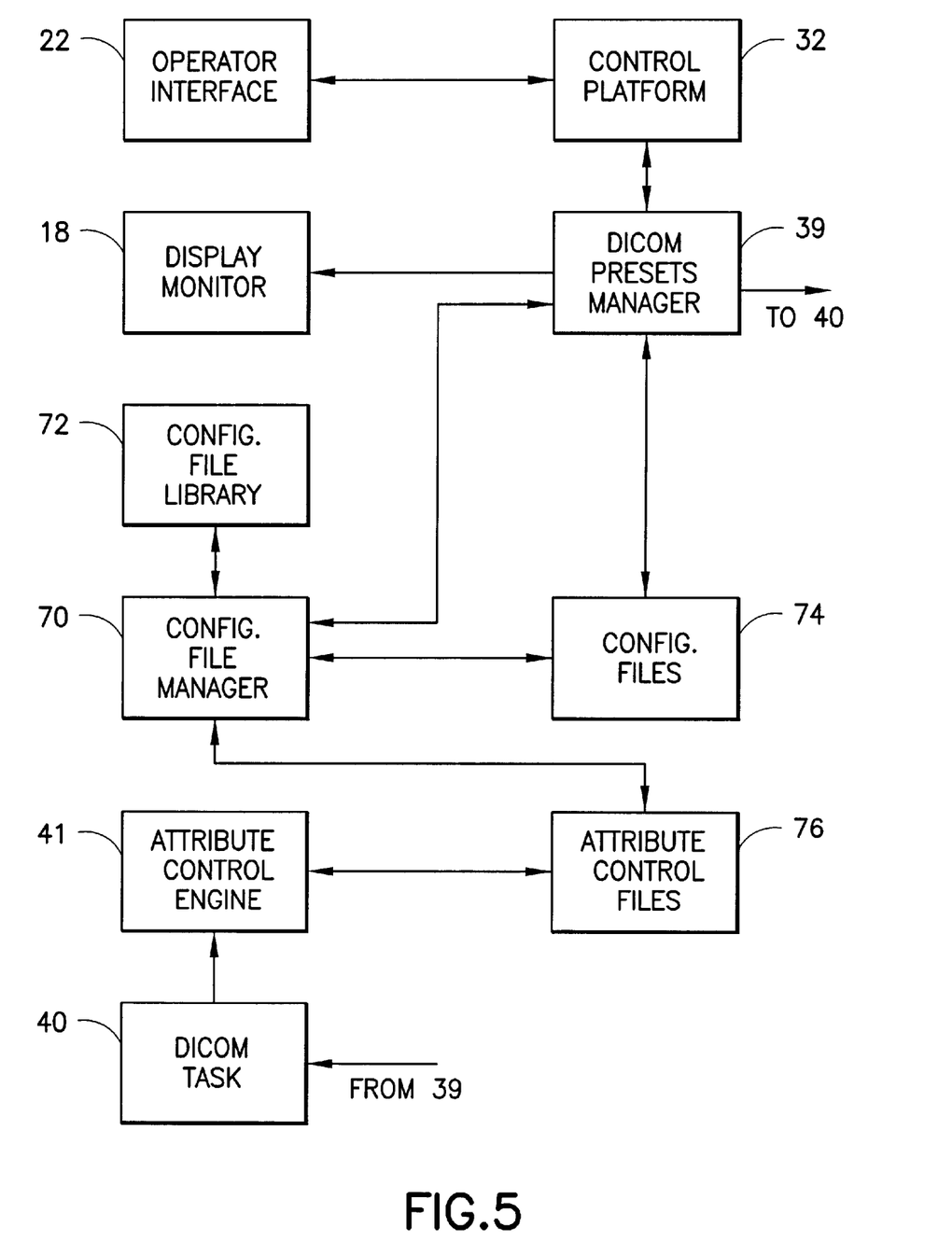
FIG. 5 is a block diagram generally depicting portions of the hardware and software of an ultrasound imaging system in accordance with the preferred embodiment of the present invention.

The imager is programmed to store configuration data inputted via the Device Configuration menu shown in FIG. 4. However, the present invention eliminates the necessity of a field engineer manually filling out the Device Configuration menu with configuration data. Instead the field engineer is able to select a prestored configuration file for the specific remote device being added, and then supplement and optionally modify the configuration data. As seen in FIG. 5, the configuration files for all makes and models of configurable devices are pre-stored on the imager hard disk (e.g., by reading from install disks) in a configuration file library 72. Naturally, as many devices as possible should be represented by corresponding configuration files in the library to ensure that there will be a match for any make and model to be added to the imager's list of configured devices.

Each configuration file comprises three sections of data in ASCII code. The format of the configuration files is as follows. The first section includes the following data items for the particular device: Vendor (i.e., make), Type, Model, Version, AE_Title, Port, and Xfer_Syntax. These items are included in Section 1 for all Device Types and appear in the portion of the Device Configuration menu (see FIG. 4). (Other items which appear in the top portion of the Device Configuration menu but which are not included in the configuration files are data items which apply to all devices, such as Retries, Retry Interval, Timeout, etc., are automatically added to the configuration file read from the library, thereby effectively creating a new configuration file.) The second section contains a different set of data items for each device type. These items appear on the Device Configuration menu under the respective headings Printer Setup, Worklist Setup and Storage Setup. For printer and storage configuration files, the third section comprises the attribute tags used by the Attribute Control Engine. For worklist configuration files, the third section comprises the items which appear on the Worklist Setup menu, an example of which is presented in FIG. 7. The format for this section is as follows:

Search field : use: display order : criteria

Figure 7:
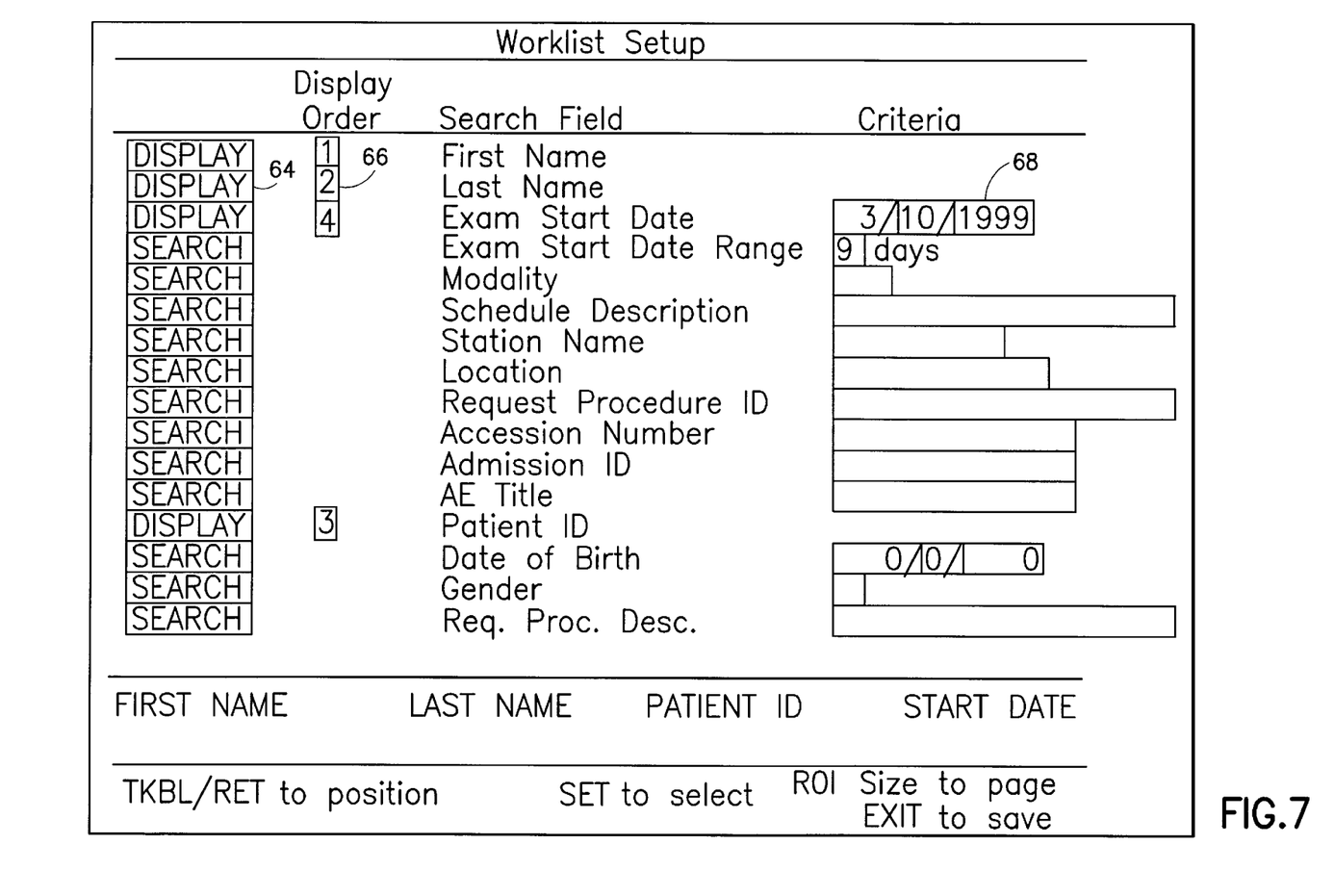
FIG. 7 is a schematic reproducing a Worklist Setup display menu which the operator interacts with during setup of a worklist query.

The term "use" refers to one of the following: SEARCH, DISPLAY, IGNORE, which are explained in detail below.

In accordance with the preferred embodiment of the invention, the field engineer uses the operator interface 22, and a graphical user interface displayed on the display monitor 18, to select a configuration file from the library 72. The graphical user interface includes a Device Configuration menu of the type shown in FIG. 4 and a DICOM Device List dialogue box of the type shown in FIG. 6.

For all devices to be installed, the field engineer needs to fill out the top portion of the Device Configuration screen shown in FIG. 4. The top portion of the screen pertains to any generic DICOM device. The type of configured device indicated in FIG. 4 is a storage server, which is identified by the term "Storage" in the Device Type field 48. The field engineer will toggle to the desired Device Type (i.e., Storage, Printer or Worklist) in field 48 by hitting the SET button on the operator interface. When the engineer leaves the Device Type field, a pop-up dialogue box or window (shown in FIG. 6) corresponding to the selected type of device will appear. The dialogue box presents a pick list 58 listing the vendor (make), model and version for each device belonging to the selected Device Type and having a corresponding configuration file in the library. In the example shown in FIG. 6, the pick list 58 comprises different storage devices. The list, if too long to appear in full in the window, can be scanned in conventional fashion by clicking on the virtual Scan Up and Scan Down buttons identified by arrowheads in FIG. 6.

In accordance with the preferred embodiment of the invention, the configuration file manager 70 receives the Device Type selection from the DICOM presets manager 39 and then searches the configuration file library 72 for all files corresponding to devices of the selected type. In addition, the configuration file manager 70 extracts the vendor, model and version data from each file identified by the search and sends that information to the DICOM presets manager 39. The DICOM presets manager 39 then constructs a list of equipment in a three-column table format and displays the list 58 on the pop-up dialogue box or window as shown in FIG. 6.

Figure 6:
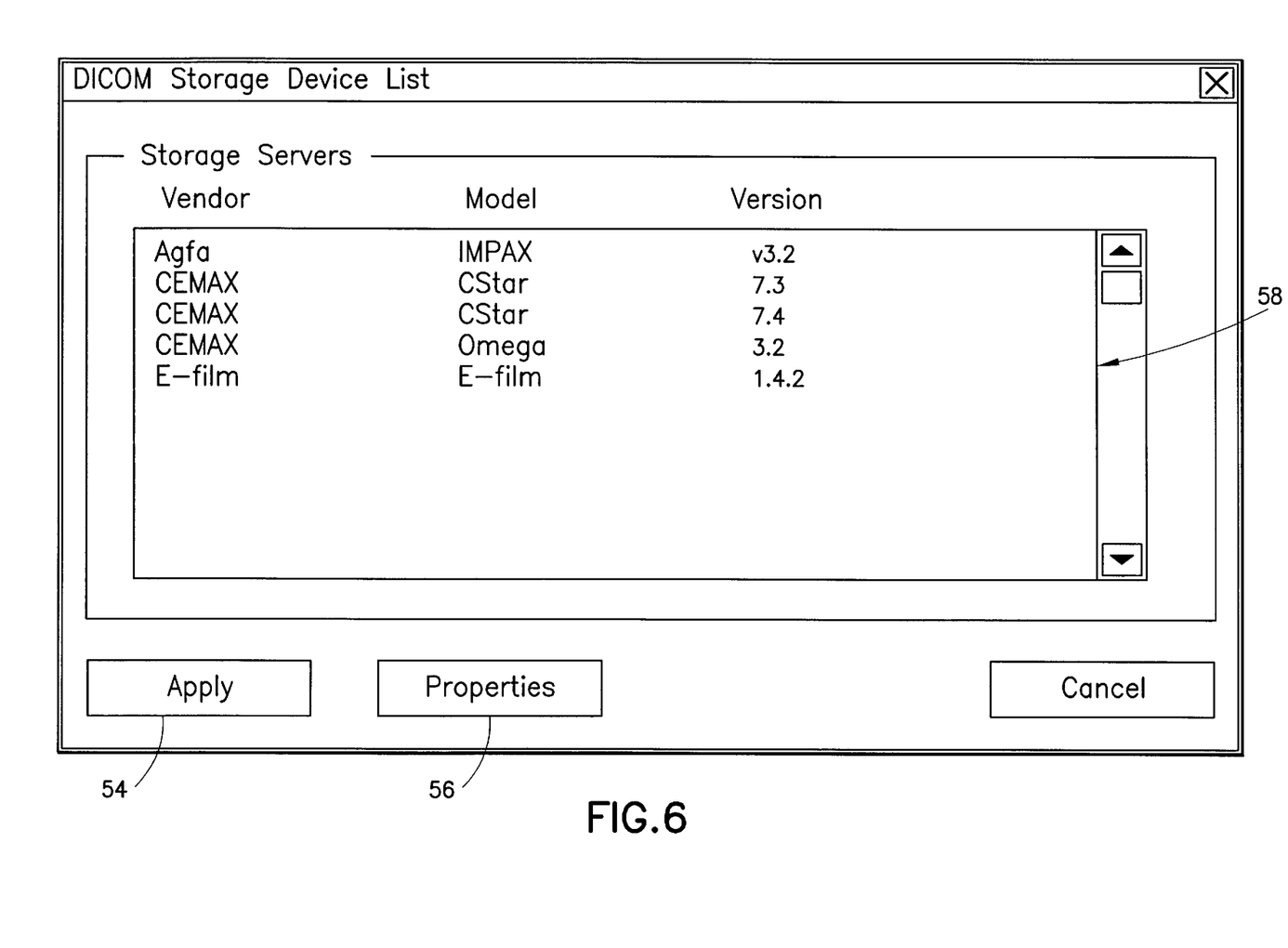
FIG. 6 is a schematic reproducing a "Device List" screen which can be used to select a prestored configuration file for loading from the hard disk to host computer memory in accordance with the preferred embodiment of the invention.

The dialogue box shown in FIG. 6 appears on the screen after the field engineer has selected the type of DICOM device to be configured. This box is the same for all devices with the exception of the labels and content. If the field engineer selects Storage as the type of the device, then this box will appear showing a list 58 of storage devices that the scanner has configuration files for. If the field engineer selects Printer for device type, then a list of printers appears. If the field engineer selects Worklist, then a list of worklist devices appear. If the field engineer is able to find on the pick list 58 the make/model of the equipment to be configured on the imager, the field engineer will select that piece of equipment by clicking on the row identifying the equipment and then clicking on a virtual Apply button 54. To use the Apply button 54, the field engineer must select a single item from the list shown. If the field engineer does not select an item, then he/she will not be able to press the Apply button. Once the field engineer selects the appropriate item, he can press the Apply button. At that time, the dialogue box disappears and the appropriate configuration file will be automatically copied to the system memory. If the field engineer would like to see more information about a selected item in the list, he can press the Properties button 56. At that time a new window will open, showing the entire configuration file. The field engineer can modify attribute data in the configuration file. The field engineer at any time can choose to exit this dialogue box, with no action taken, by pushing the Cancel button.

When the Apply button 54 has been clicked on, the dialogue box of FIG. 6 disappears and data fields in the upper portion and the lower portion (corresponding to the selected Device Type) of the Device Configuration screen are filled in automatically with data taken from Sections 1 and 2 of the copied configuration file. If the equipment is a worklist device, then the Worklist Setup portion of the Device Configuration menu (see FIG. 4) is filled out with data from Section 2 of the selected configuration file, and the worklist tags found in the Worklist Setup screen (see FIG. 7) are filled in with data from Section 3 of the configuration file. Any entry in the Device Configuration menu can be modified by the field engineer.

More specifically, the configuration file manager 70 receives the selection information from the DICOM presets manager 39 and copies Sections 1–3 of the selected configuration file from the library 72 into the system memory and adds some configuration data to form a new configuration file 74 (see FIG. 5). DICOM presets manager 39 automatically retrieves configuration data from the new configuration file 74 for display in the data fields appearing in the Device Configuration menu (FIG. 4) and the Worklist Setup screen (FIG. 7). These steps are repeated for each configured device.

When the field engineer exits the page of the Device Configuration menu which is being displayed, the corresponding configuration file 74 on the system memory will be saved to the hard disk. If the configured device has been activated (as described above), the configuration file manager 70 also uses Section 3 of each configuration file to populate an Attribute Control File and saves that Attribute Control File to the hard disk. This process is repeated for each page of the Device Configuration menu which is filled in. After all new configuration files and Attribute Control Files have been installed on the hard disk, the system is rebooted. During powering up, the host computer copies the newly installed files to system memory for use during system operation.

The Attribute Control File 76 shown in FIG. 5 represents the file on the system memory, not the file as stored on the hard disk. The Attribute Control File tells the imager which DICOM tags to use for a particular receiving device. Further, it allows the system to be configured in such a way that the system does not have to follow the DICOM standard. In other words, it allows the remapping of tags to other tags, the forcing of information in a particular tag, and the removal or addition of a tag or group of tags. The Attribute Control Engine 41 retrieves attributes from the Attribute Control File 76. If the equipment being added is configured but not activated, then a configuration file 74 will be stored on system memory for that equipment, but an Attribute Control File will not. The equipment will be listed on the Device Activation screen (see FIG. 8) as having an inactive status.

After the imager has been configured, images can be transferred to configured and activated remote devices. The image transfer procedure will be described with reference to FIG. 3. In response to a request from the operator to archive a frozen image, the control platform 32 sends an "Image Store" instruction to the archive manager 34. In response to the "Image Store" instruction, the archive manager retrieves the frozen image from cine memory 16 and stores it either on the hard disk 36 or on the MOD 46, depending on the system operator's selection.

In addition, the system operator may request that the frozen image be sent to an activated remote device for printing or storage by pressing the appropriate Print/Store button. In response to a request from the operator to transfer a frozen image to a remote device, the control platform 32 sends an "Image Send" instruction to the archive manager 34. The archive manager 34 retrieves the frozen image from the cine memory 16 and stores it in a file on the hard disk 36. The file includes the image pixel data as well as certain attribute data, such as patient name, patient ID, gray-scale or color image, number of rows and columns of pixels, etc. Then the archive manager 34 notifies the DICOM queue manager 38 of the image to be transferred and the destination remote device that image (and subsequent images of the same job) will go to. Next the queue manager 38 copies the image to another location on the hard disk and gives that copied image a new file name. If the pressed Print/Store button is configured for multiple remote devices, then the queue manager 38 will store multiple copies of the frozen image in multiple files, i.e., a separate copy of the frozen image for each remote device designated as a destination for that image.

In accordance with the DICOM standard, each DICOM task is designed to convert an image file, comprising image frame data and attribute data, into a DICOM-formatted object, also comprising image frame and attribute data. That DICOM object must conform not only to the DICOM standards, but also to the attribute requirements of the remote device destined to receive that DICOM object. Each DICOM task 40 constructs DICOM objects by associating attribute names and values with attribute tags identified in a selected one of a pair of Attribute Control Files as being compatible with the destination remote device. The Attribute Control Engine 41 controls which attributes to include and which attribute names and values to associate with which attribute tags in the DICOM objects constructed by each DICOM task 40. When the system is powered up, the Attribute Control Engine 41 reads the Attribute Control Files from the hard disk 36 and writes them into system memory. These Attribute Control Files are kept in system memory for the duration of the power cycle. Each Attribute Control File comprises many lines for setting up the DICOM attributes. One line is needed to set up one DICOM attribute. The format of each line is as follows:

[Module Name][Tag Number][Sequence Number][Format String]

The module name specifies the DICOM module which the attribute on that line belongs to. The module name is a defined term. The tag number specifies a particular attribute included in that module. Some DICOM attributes have the sequence of the subset of some DICOM attributes. The sequence number specifies the sequence which the attribute belongs to. The format string specifies how the data value of the attribute should be created.

Each DICOM task 40 must receive instructions from the Attribute Control Engine 41 concerning which attributes to include and which attribute tags to use in the DICOM object being constructed by that DICOM task, the tags being the tag numbers stored in the selected Attribute Control File. First, the DICOM task 40 asks the Attribute Control Engine 41 whether a particular attribute should be included in the DICOM object. The Attribute Control Engine 41 refers to the selected Attribute Control File to determine whether the attribute should be included. If the attribute should not be included, the Attribute Control Engine 41 advises the DICOM task accordingly. The DICOM task 40 then proceeds to the next attribute. If the attribute should be included in the DICOM object under construction, the Attribute Control Engine 41 so advises the DICOM task 40. The DICOM task then asks the Attribute Control Engine 41 whether the value of that attribute should be obtained from the image file which is being converted or whether the attribute value should be obtained from the selected Attribute Control File. Again the Attribute Control Engine 41 refers to the selected Attribute Control File. If the attribute value should be taken from the image file, the Attribute Control Engine so advises the DICOM task. Alternatively, if the attribute value should be taken from the selected Attribute Control File, the Attribute Control Engine 41 retrieves that attribute value and sends it to the DICOM task 40.

The foregoing procedure is repeated for each attribute associated with the particular function, i.e., construction of a print object or storage object, being performed by a particular DICOM task. In other words, if the DICOM task is performing the storage function, then the DICOM task will query the Attribute Control Engine with regard to only those attributes which are relevant to the storage function. This is also true for the print function. In response to each query from the DICOM task 40 regarding a particular attribute, the Attribute Control Engine 41 will read only that line in the selected Attribute Control File corresponding to that attribute.

Referring again to FIG. 3, each DICOM task 40 sends its DICOM object in proper format to the corresponding destination remote device via the network manager 42 and the port 44. The DICOM tasks run concurrently and independently of each other in accordance with conventional multitasking principles. Jobs which are waiting to be converted into DICOM objects by a DICOM task are queued. The queue is managed by a DICOM queue manager 38. The first job in the queue is sent by the queue manager 38 to the DICOM task 40 identified by the Task ID and corresponding to the destination remote device for that first job. When the DICOM task 40 receives a job from the queue, it will read a pointer which contains the file name of the image to be formatted and transferred to the destination remote device. The DICOM task 40 then retrieves the image from the named file on the hard disk and reformats it into the appropriate DICOM object in accordance with the instructions from the Attribute Control Engine 41. In addition to the pixel data for the image being transferred, the DICOM object constructed by the DICOM task will include attribute data in DICOM format. If the remote device is a storage device, the DICOM task will also attach a UID to the image.

Next the DICOM task 40 will open a connection (association) to the destination remote device and negotiate a syntax. In particular, the DICOM task 40 sends a request via the network manager 42 and a port 44 that an association with the configured remote device be opened. If the remote device responds affirmatively and if a communications syntax is agreed upon, the association is opened. Once the association is open and assuming that a channel on the network is available (i.e., the network is not busy), the image is sent from the imager onto the network, again via network manager 42 and port 44. If the destination remote device sends back a message that the image transfer was successful, then the DICOM task 40 notifies the queue manager 38. The queue manager then removes the entry for the successfully transferred image from the queue and deletes that image file from the hard disk 36.

A worklist query is typically made by the system operator prior to initiation of an examination. One purpose of such a query is to retrieve patient information from a central location and annex that information to each image frozen and stored on the hard disk. The field engineer configures the system to request only selected worklist information from the central location. In accordance with the preferred embodiment of the invention, the field engineer sets up the worklist and defines the search parameters by copying the appropriate configuration file from the library. The configuration data from the copied file appears in the Worklist Setup menu shown in FIG. 7. After the worklist has been set up and the search parameters defined, the system operator can initiate a search. The DICOM task 30 then opens up an association with the RIS or other worklist broker and sends the worklist query over the network. The imager subsequently receives the requested worklist information from the remote worklist broker. If the transfer of worklist information from the remote worklist broker to the imaging system was successful, the association is then closed. The operator can then click on a particular entry in the worklist displayed on a Worklist menu (not shown), in response to which all retrieved information for that worklist entry is automatically entered into a new patient data file. The new patient data can be viewed by returning to a New Patient menu on the display screen.

Although the disclosed preferred embodiment is an ultrasound scanner which communicates with remote devices using the DICOM protocol, it should be appreciated that the invention has application in scanner of other modalities and in scanners which use communication protocols other than DICOM.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. An imaging system comprising:
    a library of configuration files stored on a hard disk, each configuration file comprising attribute configuration data for a different make/model of device, the attribute configuration data for a given configuration file comprising a respective name and an associated respective tag for each attribute that is required by a respective device to be included in a data object to be sent to said respective device by said imaging system;
    a graphical user interface comprising means for identifying a device on a network for receiving an object from said imaging system;
    a networking port for communicating with said device on said network;
    system memory storing an attribute control file; and
    a computer programmed to perform a step of copying attribute configuration data to said system memory from a configuration file in said library corresponding to said identified device in response to a first input via said graphical user interface by a system user and populating said attribute control file with said copied attribute configuration data in system memory in response to a second input via said graphical user interface by the system user.

2. The system as recited in claim 1, wherein said computer is further programmed to perform the step of sending an object to said networking port, said object being destined for said identified device and comprising attribute information configured in accordance with said copied attribute configuration data in said attribute control file.

3. The system as recited in claim 1, wherein said graphical user interface comprises a pick list listing the make and model of each of a multiplicity of devices belonging to a device type, said identified device being selected from said pick list.

4. The system as recited in claim 3, wherein said graphical user interface further comprises a menu comprising a device type field for selecting said device type from a plurality of device types, said pick list being displayed following selection of said device type.

5. The system as recited in claim 4, wherein said graphical user interface comprises means for toggling said device type field to display a successive one of said plurality of device types with each toggle.

6. The system as recited in claim 3, wherein said computer is further programmed to perform the steps of:
    retrieving said make and model from said library for each of said multiplicity of devices belonging to said device type; and
    constructing said pick list using said retrieved make and model for each of said multiplicity of devices belonging to said selected device type.

7. The system as recited in claim 6, wherein said graphical user interface further comprises a menu comprising a device type field for selecting said device type from a plurality of device types, said computer performing said retrieving and sending steps following selection of said device type.

8. The system as recited in claim 3, wherein said menu further comprises a device activation field for activating said identified device on said system.

9. The system as recited in claim 8, wherein said computer is further programmed to perform the step of
    sending an object to said networking port, said object being destined for said identified device and configured in accordance with attribute information in said attribute control file.

10. A method of configuring an imaging system to communicate with a device on a network, comprising the following steps:
    installing a library of configuration files on a hard disk of said imaging system, each configuration file comprising attribute configuration data for a different make/model of device, the attribute configuration data for a given configuration file comprising a respective name and an associated respective tag for each attribute that is required by a respective device to be included in a data object to be sent to said respective device by said imaging system;
    identifying a device on a network for receiving an object from said imaging system;
    copying attribute configuration data to system memory from a configuration file in said library corresponding to said identified device; and
    populating an attribute control file with said copied attribute configuration data in system memory.

11. The method as recited in claim 10, wherein said computer is further programmed to perform the step of sending an object to said networking port, said object being destined for said identified device and comprising attribute information configured in accordance with said copied attribute configuration data in said attribute control file.

12. The method as recited in claim 10, further comprising the step of displaying a pick list on a graphical user interface, said pick list comprising a multiplicity of device identifiers, each device identifier comprising a respective make and model of each of a multiplicity of devices belonging to a device type, wherein said identifying step is performed by selecting a device identifier from said pick list.

13. The method as recited in claim 12, further comprising the step of selecting said device type from a plurality of device types, said pick list being displayed following selection of said device type.

14. The method as recited in claim 13, further comprising the steps of:
    displaying a device type field on a graphical user interface; and
    toggling said device type field to display a successive one of said plurality of device types with each toggle, said selected device type being selected when said device type is displayed in said device type field.

15. The method as recited in claim 12, further comprising the steps of:
    retrieving said make and model from said library for each of said multiplicity of devices belonging to said device type; and
    constructing said pick list using said retrieved make and model for each of said multiplicity of devices belonging to said selected device type.

16. An imaging system comprising:
    a library of configuration files stored on a hard disk, each configuration file comprising attribute configuration data for enabling the imaging system to communicate with a different make/model of device, the attribute configuration data for a given configuration file comprising a respective name and an associated respective tag for each attribute that is required by a respective device to be included in a data object to be sent to said respective device by said imaging system;

a graphical user interface comprising means for identifying a device for receiving an object from said imaging system via a network;

a networking port for communicating with said device via said network;

system memory storing an attribute control file; and a configuration file manager programmed to copy attribute configuration data to said system memory from a configuration file in said library corresponding to said identified device in response to a first input via said graphical user interface by a system user and populating said attribute control file with said copied attribute configuration data in system memory in response to a second input via said graphical user interface by the system user.

17. The system as recited in claim 16, further comprising means for sending an object to said networking port, said object being destined for said identified device and comprising attribute information configured in accordance with said copied attribute configuration data in said attribute control file.

18. The system as recited in claim 16, further comprising a display monitor, wherein said input device comprises a user-interactive pick list displayed on said display monitor, said pick list listing the make and model of each of a multiplicity of devices belonging to a device type, said identified device being selected from said pick list.

19. An apparatus for configuring an imaging system, comprising:

a library of configuration files stored on a hard disk, each configuration file comprising attribute configuration data for enabling the imaging system to communicate with a different make/model of device, the attribute configuration data for a given configuration file comprising a respective name and an associated respective tag for each attribute that is required by a respective device to be included in a data object to be sent to said respective device by said imaging system;

a graphical user interface comprising: a menu comprising a device type field which is activatable to select a device type from a plurality of device types; a pop-up screen which is displayed on said menu when a device type is selected, said pop-up screen displaying a listing of the make and model of each of a multiplicity of devices belonging to said selected device type; and a virtual button which is activatable to select a make and model of a device in said listing;

system memory storing an attribute control file; and a configuration file manager programmed to copy attribute configuration data to said system memory from a configuration file in said library corresponding to said selected make and model, and then populate said attribute control file with said copied attribute configuration data in system memory when the system user exits said menu if said device has been activated.

20. A method of configuring an imaging device to communicate with diverse devices, comprising the steps of:

recording a library of configuration files on an installation disk, each configuration file comprising attribute configuration data for a different make/model of device, the attribute configuration data for a given configuration file comprising a respective name and an associated respective tag for each attribute that is required by a respective device to be included in a data object to be sent to said respective device by said imaging system;

inserting said installation disk in said imaging system;

copying said library of configuration files from said installation disk onto a hard disk of said imaging system;

identifying a plurality of devices to be activated for receiving objects from said imaging system; and for each of said activated devices, populating a respective attribute control file in system memory with attribute configuration data copied from a respective configuration file in said library.

21. The method as recited in claim 20, wherein said copied attribute configuration data comprises attribute tags defined in accordance with Digital Imaging and Communications in Medicine (DICOM) standards for each of said activated devices.

* * * * *